United States Patent [19]

Yoda et al.

[11] 4,240,889

[45] Dec. 23, 1980

[54] ENZYME ELECTRODE PROVIDED WITH IMMOBILIZED ENZYME MEMBRANE

[75] Inventors: Kentaro Yoda, Otsu; Rintaro Urakabe, Shiga; Toshio Tsuchida, Otsu, all of Japan

[73] Assignee: Toyo Boseki Kabushiki Kaisha, Japan

[21] Appl. No.: 6,070

[22] Filed: Jan. 24, 1979

[30] Foreign Application Priority Data

Jan. 28, 1978 [JP] Japan ................................ 53/8590

[51] Int. Cl.³ .............................................. C12Q 1/26
[52] U.S. Cl. ............................ 204/195 B; 204/195 P; 435/817
[58] Field of Search ................ 204/195 B, 195 P, 1 E; 435/817

[56] References Cited

U.S. PATENT DOCUMENTS

| | | | |
|---|---|---|---|
| 3,539,455 | 11/1970 | Clark | 204/195 P |
| 3,542,662 | 11/1970 | Hicks et al. | 204/195 P |
| 3,979,274 | 9/1976 | Newman | 204/195 B |
| 4,073,713 | 2/1978 | Newman | 204/195 B |

FOREIGN PATENT DOCUMENTS 1442303  7/1976  United Kingdom ................ 204/195 P Primary Examiner—G. L. Kaplan
Attorney, Agent, or Firm—Jones, Tullar & Cooper

[57] ABSTRACT

An enzyme electrode comprising an anode, a cathode, an immobilized enzyme membrane, and an electrolyte, which is characterized in that said membrane consists of a dense skin layer having selective hydrogen peroxide permeability and a porous layer wherein the enzyme is immobilized onto the porous layer of the membrane and said immobilized enzyme membrane is arranged in the electrode so that the skin layer is faced to the electrode and the porous layer immobilized with the enzyme is in the position of contacting with the test solution. The enzyme electrode is used for the polarographic determination of a slight amount of components in body fluid, body tissue, foodstuffs, or the like without any undesirable hindrance with low molecular interfering materials without using any other specific means for removing such low molecular interfering materials.

3 Claims, 3 Drawing Figures

ENZYME ELECTRODE PROVIDED WITH IMMOBILIZED ENZYME MEMBRANE

BACKGROUND OF THE INVENTION

The present invention relates to a polarographic cell provided with an immobilized enzyme membrane. More particularly, it relates to an enzyme electrode for detecting hydrogen peroxide comprising an anode, a cathode, an immobilized enzyme membrane having a specific structure and an electrolyte, said immobilized enzyme membrane being arranged facing to the anode.

There are widely used methods for determining selectively a slight amount of various components such as glucose, urea, uric acid, triglycerides, phospholipids, creatinine, amino acids, lactic acid, xanthine, chondroitin, transaminase, etc. which are contained in body fluid, body tissue, foodstuffs, or the like.

Generally, enzymes have a specificity against a substrate thereof and act selectively thereon under mild conditions, and hence, they are advantageously employed for the determination of such components as mentioned above without using any specific reagent and also without any problem of environmental pollution. The enzymes have, on ther other hand, some drawbacks that they are chemically and physically unstable and the process of the determination is so complicated. In order to eliminate the drawbacks, it has been proposed to immobilize the enzyme. Besides, it has also been proposed to employ the immobilized enzymes in a polarography which is useful for the electrical determination of components contained in a slight amount in test samples (cf. Japanese Patent Publication No. 28672/1972). That is, an enzyme electrode provided with an immobilized enzyme membrane is contacted with a solution to be analyzed, by which the enzyme is reacted with the substrate to produce an electrode detectable substance, e.g. hydrogen peroxide, and the resulting detectable substance is detected with an electrode cell. In this manner, the component contained in the test solution is polarographically analyzed. When the electrode detectable substance is hydrogen peroxide, the hydrogen peroxide is decomposed with the anode, whereby an electric current flows through the polarographic cell in proportion to the amount of hydrogen peroxide. Since the value of electric current is proportionate to the amount of the component to be determined, the amount of the component can be calculated. In practice of this method, however, it is necessary to previously remove the interfering materials contained in the test solution, which are active to the polarography. For instance, when glucose contained in blood is determined, other components active to the polarography, such as uric acid, ascorbic acid, glutathione, mercaptoacetic acid, etc., should previously be removed. In order to correct the error due to these interfering materials, it has been proposed to employ a multiple electrode system, whereby the signal owing to the interfering materials is corrected (cf. Japanese Patent Publication No. 35360/1970). This system has, however, complicated electrode constituents and electrical circuit, and hence, this system is disadvantageously expensive and troublesome in the operation thereof. It has also been proposed to employ a laminate membrane comprising a membrane which can selectively permeate the detectable substance, an immobilized enzyme membrane and a membrane for removing high molecular materials in order to eliminate low molecular weight interfering materials of (cf. Japanese Patent Laid Open Publication (unexamined) No. 55691/1977). However, it is troublesome to laminate and adhere multiple membranes uniformly and precisely, which requires a highly trained technique. Moreover, the laminate membrane has a low strength and is easily broken and shrunk, and hence, it is difficult to install onto the electrode or to take off therefrom. It has also been proposed to employ a porous membrane (cf. Japanese Patent Laid Open Publication (unexamined) No. 17889/1977). However, when the porous membrane has a small pore diameter, it shows a good selective permeability of the detectable substance, but the contact of the substrate and the enzyme becomes insufficient, which induces inaccurate results of the determination. On the other hand, when the porous membrane has a large pore diameter, the selective permeability becomes insufficient and the interfering materials also permeate, which induces inaccurate results of the determination, too.

DETAILED DESCRIPTION OF THE INVENTION

Figure 1:
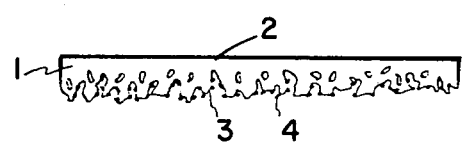
FIG. 1 shows a model, sectional view of the immobilized enzyme membrance of the invention.

As the result of the present inventors' intensive study, it has been found that the drawbacks in the known methods or apparatuses as mentioned above can be eliminated by using a specific membrane having such a specific structure that one surface thereof facing to the electrode is plain and permeates selectively hydrogen peroxide but does not permeate the substrate and the interfering materials, and another surface thereof facing to and contacting with the test solution is rough and porous, and the enzyme being immobilized onto the rough and porous surface of the membrane.

An object of the present invention is to provide an enzyme electrode provided with an immobilized enzyme membrane having a specific structure. Another object of the invention is to provide an improved immobilized enzyme membrane useful for polarographic analysis of a slight amount of components. A further object of the invention is to a method for the determination of a slight amount of components by detecting hydrogen peroxide produced or consumed by the reaction of an enzyme and the substrate with a polarographic cell comprising an anode, a cathode, an immobilized enzyme membrane having a specific structure and an electrolyte, said immobilized enzyme membrane being arranged facing to the anode. These and other objects of the present invention will become apparent from the following description.

The immobilized enzyme membrane of the present invention has such a specific structure that one surface thereof facing to the electrode is dense and forms a plain skin layer which shows a selective permeability and can permeate only hydrogen peroxide and another surface of the membrane is porous and the enzyme is immobilized into the pores of the porous surface. The enzyme-immobilized surface is contacted with the test solution, and the substrate is penetrated into the pores and therein is reacted with the enzyme to produce hydrogen peroxide.

The immobilized enzyme membrane of the present invention has an excellent selective permeability and can completely prevent the undesirable permeation of low molecular weight interfering materials and also shows excellent contact of the enzyme and the substrate, and hence, the enzyme electrode provided with the immobilized enzyme membrane is useful for the accurate determination of a slight amount of components in body fluid, body tissue, foodstuffs, or the like. The immobilized enzyme membrane has further many advantages, such that (1) it has a high membrane strength and is easily handled; (2) since it is a single layer (not laminated product), it is uniform and even and there can be obtained accurate determination data with good reproducibility; (3) it can be produced in a low cost; (4) because of the good penetration of the substrate, the measurement can be done within a short period of time; and (5) there is no carry-over.

The immobilized enzyme membrane and enzyme electrode of the present invention are described in more detail with reference to the accompanying drawings.

FIG. 1 shows a model, sectional view of the immobilized enzyme membrane of the present invention. As is shown in FIG. 1, the immobilized enzyme membrane 1 has one surface 2 which is to be faced to the electrode and forms a dense skin layer, and has another surface 3 which is to be faced to the test solution and is rough and porous. The enzyme 4 is immobilized onto the porous surface, particularly into the pores on the porous surface 3.

Figure 2:
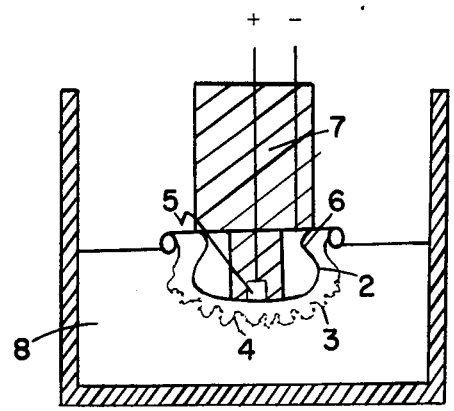
FIG. 2 shows a model, sectional view of an enzyme electrode for polarography provided with the immobilized enzyme membrane of the invention.

FIG. 2 shows a model, sectional view of an enzyme electrode for polarography provoded with the immobilized enzyme membrane of the present invention, wherein 5 is an anode, 6 is a cathode, 7 is an insulated support for supporting the electrode, and 8 is an electrolyte, i.e. a test solution. As is shown in FIG. 2, the immobilized enzyme membrane 1 of the present invention is arranged in the polarographic cell so that the surface 2 faces to the electrode and the porous surface 3 is contacted with the test solution to be analyzed. At the porous surface 3, the enzyme 4 immobilized onto the porous surface is reacted with the substrate contained in the test solution to produce an electrode detectable substance, i.e. hydrogen peroxide, and the hydrogen peroxide thus produced permeates the immobilized enzyme membrane 1 and is decomposed with the anode 5, whereby the amount of hydrogen peroxide is polarographically determined. The anode is usually made of platinum, but may also be made of gold. The cathode is usually made of silver, but may also be made of silver-silver chloride.

The membrane is made of high molecular compounds, i.e. homopolymers or copolymers such as polyamides, polyurethanes, cellulose acetate, cellulose, polyethylenimine, polyvinyl alcohol, polycarbonates, polymethyl methacrylate, or polyacrylonitrile. Preferred high molecular compounds are hydrophilic high molecular compounds such as polyamides, cellulose acetate, or polyvinyl alcohol.

The membrane having a specific structure can be prepared by various methods. For instance, the starting high molecular compound is dissolved in a solvent (e.g. acetone), and the dope thus prepared is casted into a thin film onto a base plate having a smooth surface, such as a glass plate, plastic plate or metallic plate, the solvent is evaporated within a short period of time to form a skin layer having a selective permeability on the base plate, and then the resulting membrane is dipped in a solvent which can hardly or little dissolve the high molecular compound, by which the high molecular compound-soluble solvent contained in the membrane is removed to form a porous layer adjacent to the skin layer (cf. Japanese Patent Laid Open Publication (unexamined) No. 94482/1976 and U.S. Pat. Nos. 3,133,132 and 3,133,133). The membrane can also be prepared by preparing a porous membrane having continuous pores from the starting high molecular compound by conventional methods, such as elution, casting, drawing, or the like, treating one surface of the porous membrane thus produced with a solvent which can dissolve the starting high molecular compound, and thereby forming the skin layer on the surface (cf. Japanese Patent Laid Open Publication (unexamined) No. 69476/1977). Alternatively, the membrane may be prepared by forming a thin layer on one surface of a porous membrane by subjecting the porous membrane to a plasma polymerization in an inert gas (cf. J. R. Hollaman, T. Wydeven; J. Appl. Polymer Sci., Vol. 21, 923 (1977) and Japanese Patent Publication No. 32755/1977). The membrane may also be prepared by forming a membrane of a high molecular compound, which does not occur any fine crack by drawing thereof, on one surface of a membrane of a high molecular compound, which occurs fine cracks by drawing thereof, and then drawing the resulting two layer membrane to produce many fine cracks on the above latter membrane (cf. Japanese Patent Laid Open Publication (unexamined) Nos. 119069/1976, 135974/1976 and 135975/1976).

The membrane has preferably a thickness of 5 to 50 $\mu$m, more preferably 10 to 20 $\mu$m. The skin layer of the membrane having an excellent selective permeability (the substrate being not permeated and only the hydrogen peroxide being permeated) has preferably a thickness of not more than about 5 $\mu$m, particularly not more than 1 $\mu$m. Particularly preferred thickness of the skin layer is in the range of 0.5 to 1 $\mu$m.

The enzyme to be immobilized onto the porous surface of the membrane includes various oxidoreductases which can react with the substrate to release hydrogen peroxide or can consume hydrogen peroxide by an enzymatic reaction, such as glucose oxidase, galactose oxidase, uricase, cholesterol oxidase, choline oxidase, l-amino acid oxidase, d-amino acid oxidase, xanthine oxidase, alcohol oxidase, aldehyde oxidase, lactic acid oxidase, pyruvic acid oxidase, or peroxidase. There may also be used enzymes or coenzymes which do not directly release or consume hydrogen peroxide by an enzymatic reaction but produce a substrate for an enzymatic reaction with production or consumption of hydrogen peroxide, such as lipase, lipoprotein lipase, phospholipase, cholesterol esterase, $\beta$-galactosidase, or mutarotase. Microorganisms or organelles which contain enzymes may be immobilized instead of the enzymes themselves.

Immobilization of the enzyme onto the membrane can be done by conventional methods. For instance, according to chemical bonding methods such as a covalent bonding method, ionic bonding method, or crosslinking method, the enzyme is bound to amino group, hydroxy group or the like contained in the membrane-constituting substance via a crosslinking agent such as glutaraldehyde or hexamethylene diisocyanate; or the enzyme is immobilized by the direct reaction of carboxyl group contained in the enzyme and an amino group or other reactive group contained in the membrane-constituting substance; or the enzyme is immobilized by firstly activating hydroxy group contained in the membrane-constituting substance by modification with an acid azide, or by imidocarbonation or carbonation thereof and then reacting the enzyme therewith. Alternatively, the enzyme can be immobilized by a physical adsorption method, for instance, by penetrating a carrier (e.g. kaolinite, calcium phosphate gel, starch, gluten, etc.) into the porous surface of the membrane and then penetrating the enzyme therein, or by penetrating directly the enzyme into the porous surface. Moreover, the enzyme may be immobilized by penetrating a mixture of an enzyme with a high molecular compound having an active group (e.g. amino, hydroxy, or carboxyl group) such as polyamides, cellulose, or polyacrylic acid into the porous surface of the membrane and then crosslinking the enzyme with a crosslinking agent (e.g. glutaraldehyde or hexamethylene diisocyanate); or by penetrating an enzyme solution into the porous surface of the membrane and then directly crosslinking the enzyme to the membrane with the crosslinking agent as mentioned above; or by penetrating a mixture of an enzyme and a high molecular compound such as protein or chitosan into the porous surface of the membrane and then gelating the mixture by treating it with an alkali.

The immobilization of enzyme may be carried out simultaneously when the membrane is formed or after forming of the membrane. When another enzyme or coenzyme is used together, it may be dissolved in the test solution to be analyzed or may be immobilized to the membrane together with the main enzyme.

The immobilized enzyme membrane of the present invention is provided in the conventional polarographic cell, which comprises a platinum anode, a silver silver chloride cathode and a potassium chloride electrolyte, or comprises a platinum anode, a silver cathode and a sodium acetate electrolyte. Other polarographic cells may also be used.

The immobilized enzyme membrane of the present invention has excellent selective permeability, stability and enzymatic activity, and hence, the enzyme electrode provided with the immobilized enzyme membrane is useful for the determination of a slight amount of components contained in blood, urine, body tissues, foodstufs, or the like. According to the enzyme electrode, the determination can be done in high accuracy and at a low cost within a very short period of time by using a small amount of the test sample.

The enzyme electrode provided with the immobilized enzyme membrane of the present invention is also useful for the continuous monitoring of blood sugar value. In this case, however, when the immobilized enzyme membrane is contacted with the blood sample for a long period of time, some components of blood occasionally adhere onto the membrane, which results in lowering of the performance of the membrane. In order to avoid such an undesirable phenomenon, it is preferable to cover the surface of the immobilized enzyme membrane with a porous protecting membrane having an anticoagulative property. This porous membrane should have an excellent substrate permeability and has preferably a pore diameter of 0.01 to 0.5 μm. This porous membrane is made of anticoagulative substances, such as polyurethane, polyamides, polyvinyl alcohol, cellulose acetate, polycarbonates, silicon, polyesters modified with heparin.

The present invention is illustrated by the following Examples but is not limited thereto.

EXAMPLE 1

Cellulose acetate (2 g) was dissolved in a mixed solvent (50 ml) of acetone (30 ml) and cyclohexanone (20 ml) and the mixture was flowed onto a glass plate with a knife coater in the form of a film having a thickness of 300 μm. After allowing to stand in air for 10 minutes, the product was immersed in n-hexane in order to extract the solvent. After air-drying, the film thus formed was peeled off from the glass plate to give a white membrane having a thickness of 13 μm. The membrane thus obtained comprised a dense skin layer (1 μm) and a porous layer, and the skin layer could easily permeate hydrogen peroxide but did entirely not permeate uric acid, ascorbic acid and glucose, which was confirmed by a membrane permeability test.

Separately, glucose oxidase (50 IU/mg, 25 mg), a pore-forming agent (50 mg) and alubumin (75 mg) were dissolved in a 0.05 M sodium acetate buffer (pH 5.1, 8 ml), and to the mixture was added a 25% aqueous glutaraldehyde solution (0.3 ml) to give an enzyme solution.

The enzyme solution thus obtained was penetrated into the porous surface of the membrane obtained above. By allowing the membrane thus treated to stand at 5° C. for 8 hours, the immobilization of the enzyme onto the porous surface of the membrane was completed. The immobilized enzyme membrane was washed with sodium acetate buffer and air-dried.

The immobilized enzyme membrane thus obtained was arranged into a Clarke's hydrogen peroxide electrode, so that the skin layer faced to the electrode at the head part of the electrode and the porous layer immobilized with the enzyme became in the position of the opposite side of the electrode (i.e. in the position of contacting with the test solution) as shown in FIG. 2.

Figure 3:
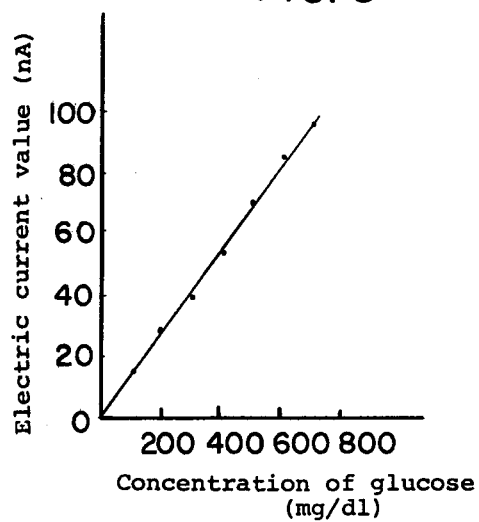
FIG. 3 is a graphic presentation of the electrode characteristics determined in Example 1.

The enzyme electrode thus obtained was immersed in a cell containing a 0.05 M phosphate buffer (pH 7.0, 0.5 ml), and thereto was added with agitation a glucose standard solution (100–700 mg/dl, 10 μl) with a micropipette. By using a polarograph (YSI type 25, oxidase meter) which was connected to the above electrode, there were measured the electric current owing to hydrogen peroxide produced by the enzymatic reaction and the variability with time. The electric current became a constant value after 20 seconds. The accompanying FIG. 3 shows a relation between the electric current value at maximum before it became at a constant value (ordinate axis) and the concentration of glucose standard solution (abscissae axis). As is clear from FIG. 3, there is a good straight relation between the concentration of glucose and the electric current value, and hence, it is possible to determine unknown concentration of glucose.

When a solution (10 μl) containing uric acid (100 mg/dl) and ascorbic acid (100 mg/dl) was added to the cell instead of the glucose standard solution, no reaction at the electrode was observed. It was confirmed by this test that the enzyme electrode of this example was not hindered with polarographically active interfering materials.

EXAMPLE 2

By using the same enzyme electrode as used in Example 1, human blood sample (10 μl) was added to the cell instead of the glucose standard solution, and the concentration of glucose in human blood was measured in the same manner as in Example 1. Based upon the calibration curve obtained for the glucose standard solution, it was calculated the blood sugar value of the test sample (175 mg/dl).

The same blood sample (10 μl) was added to a phosphate buffer (0.5 ml) containing uric acid (10 mg/dl) and the mixture was treated likewise. As the result, it showed blood sugar value of 172 mg/dl. It was clear from this result that the interfering material, uric acid did not give any effect on the measurement.

EXAMPLE 3

Polyhydroxyethyl methacrylate (5 parts by weight) which was prepared by polymerizing hydroxyethyl methacrylate in benzene using benzoyl peroxide as the initiator, methyl ethyl ketone (90 parts by weight) and isopropyl alcohol (5 parts by weight) were mixed to obtain a polymer solution. The polymer solution thus obtained was flowed onto a smooth glass plate with a knife coater in a thickness of 150 μm. After air-drying at room temperature for 10 minutes, the resulting product was immersed in a cold water and the film was peeled off from the glass plate to give a milky white, clear membrane having different surfaces and a thickness of 7.9 μm.

An aqueous choline oxidase solution was penetrated into the pores of the porous surface of the asymmetric membrane obtained above. The membrane thus treated was air-dried and washed with a potassium phosphate buffer (pH 7.5). The aqueous choline oxidase solution was prepared by dissolving choline oxidase (6.2 IU/mg, 10 mg), bovine serum alubumin (20 mg) and a 25% aqueous glutaraldehyde solution (0.05 ml) in a 0.05 M potassium phosphate buffer (pH 7.5, 2 ml).

The immobilized choline oxidase membrane obtained above was provided into a Clarke's hydrogen peroxide electrode having a platinum anode and a silver cathode in the same manner as described in Example 1.

Human blood serum (10 μl) was added to a potassium phosphate buffer (pH 7.5, 1 ml) containing phospholipase D (6.5 IU/mg, 0.5 mg), and the mixture was heated at 37° C. for 10 minutes, whereby phospholipids contained in the blood serum were hydrolyzed to give free choline. The mixture was transferred to the polarographic cell, wherein hydrogen peroxide produced by the oxidation of choline due to the enzymatic reaction (37° C.) with the enzyme electrode was polarographically measured. Based upon a calibration curve obtained previously from choline chloride standard solution (1-1000 mg/dl), the amount of phospholipids contained in the test blood serum was calculated. As the result, 281 mg/dl of phospholipids was contained. When the same blood serum was tested by a conventional Hoeflmayer-Fried method, the content of phospholipids was 285 mg/dl. Both data were well coincident.

EXAMPLE 4

Polymetaphenyleneisophthalamide (relative viscosity ($\eta_{rel}$) of 1% by weight solution in dimethylacetamide: 1.47 at 30° C., 10 parts by weight), dimethylacetamide (85 parts by weight) and lithium chloride (5 parts by weight) were mixed. The mixture was flowed onto a smooth glass plate with a knife coater in a thickness of 100 μm. After allowing to stand in an oven of 100° C. for 2 minutes while keeping horizontally, the coated glass plate was immersed in a cold water. The film thus formed was peeled off from the glass plate to give a milky white, clear membrane having different surfaces and a thickness of 11.2 μm.

An enzyme solution was penetrated into the pores of the porous surface of the asymmetric membrane obtained above and the membrane thus treated was air-dried. The enzyme solution was prepared by dissolving uricase (3.5 IU/mg, 20 mg) and chitosan (100 mg) in a 2% aqueous acetic acid solution (5 g).

The uricase-containing membrane obtained above was immersed in a borate buffer (pH 10) and then in a borate buffer (pH 9), by which the immobilization of enzyme was completed.

The immobilized uricase membrane thus obtained was provided into a Clarke's hydrogen peroxide electrode having a platinum anode and a silver cathode at the head part thereof in the same manner as described in Example 1, and the resulting enzyme electrode was immersed in a cell containing a borate buffer (pH 8.4, 20 ml) at 35° C.

Human blood serum (1 ml) was added with agitation to the cell with a micropipette, wherein hydrogen peroxide produced by the enzymatic reaction was polarographically measured. Based upon a calibration curve obtained previously from uric acid standard solution (1-100 mg/dl), the amount of uric acid contained in the test blood serum was calculated. As the result, 9.0 mg/dl of uric acid was contained. When the same blood serum was tested by a conventional uricase direct ultraviolet spectrophotometry, the content of uric acid was 8.8 mg/dl. Both data were well coincident.

EXAMPLE 5

Sulfonated polyphenylene oxide (degree of sulfonation: 1.12 mg equivalent/1 g of polymer, 5 parts by weight), chloroform (90 parts by weight) and isopropyl alcohol (5 parts by weight) were mixed. The polymer solution thus obtained was coated onto a smooth glass plate with a knife coater in a thickness of 150 μm. After air-drying at room temperature for 3 minutes, the coated plate was immersed in methanol. The film thus formed was peeled off from the glass plate to give a milky white, clear membrane having different surfaces and a thickness of 7.7 μm.

Glucose oxidase was immobilized onto the asymmetric membrane obtained above in the same manner as described in Example 1. The immobilized enzyme membrane was provided into an electrode likewise. The same sample as used in Example 2 was tested. As the result, the blood sugar value was 173 mg/dl, which was well coincident with the result in Example 2.

EXAMPLE 6

Polypropylene and nylon 66 (mixed ratio, 50:50 by weight) were kneaded, and a film having a thickness of 30 μm was prepared from the polymer mixture by melt coating method. The film was orientated by uniaxially drawing in two-fold length at 130° C., whereby cracking of the film occurred simultaneously. One surface of the film thus orientated was exposed to a vapor of n-hexane at 100° C. for 10 minutes, washed with water and air-dried to give a membrane having different surfaces and a thickness of 20 μm.

Uricase was immobilized onto the asymmetric membrane obtained above in the same manner as described in Example 4. The immobilized enzyme membrane was provided into an electrode likewise. The same sample as used in Example 4 was tested. As the result, the blood serum contained 8.5 mg/dl of uric acid, which was well coincident with the result in Example 4.

EXAMPLE 7

Nylon 6 (relative viscosity of a 1% by weight solution in 96% sulfuric acid: 3.41 at 30° C., 5 parts by weight), formic acid (90 parts by weight) and lithium chloride (5 parts by weight) were mixed, and the resulting polymer solution was flowed onto a clean smooth glass plate in a thickness of 150 μm. After allowing to stand in an oven at 100° C. for 5 minutes while keeping horizontally, the coated plate was immersed in cold water, and the film thus formed was peeled off from the glass plate to give a milky white, clear membrane having different surfaces and a thickness of 8.7 μm.

The porous surface of the membrane thus obtained above was activated by treating it with dimethyl sulfate at 100° C. for 3 minutes, and then was washed with methanol and dried under reduced pressure. The activated surface of the membrane was immersed in a 0.1 M aqueous lysine solution (pH 9.5) for 2 hours and then washed with a 0.5 M aqueous sodium chloride solution. Subsequently, the membrane was further treated with a 2.5% glutaraldehyde solution in a 0.1 M sodium borate (pH 8.5), washed with methanol and then dried under reduced pressure.

Onto the membrane introduced with aldehyde group was flowed a solution of cholesterol oxidase (10 IU/mg, 6.25 mg) in a 0.05 M phosphate buffer (pH 7.0, 1 ml). After reacting at 4° C. for 12 hours, the membrane was kept at room temperature for 5 hours and washed with phosphate buffer to give an immobilized enzyme membrane.

The immobilized enzyme membrane obtained above was provided into a hydrogen peroxide electrode so that the skin layer of the membrane faced to the electrode. The enzyme electrode was immersed in a 0.05 M sodium acetate buffer (pH 5.1, 350 μl) at 37° C., and thereto was added human blood containing known amount of free cholesterol (201 mg/dl), and then the content of free cholesterol was polarographically measured. As the result, the content of the free cholesterol was 197 mg/dl.

What is claimed is:

1. In an enzyme electrode useful for a polarographic determination of a slight amount of component in a test solution comprising an anode, a cathode, an immobilized enzyme membrane and an electrolyte, the improvement comprising an immobilized enzyme membrane consisting of a dense skin layer and a porous layer wherein the enzyme is immobilized onto the porous layer of the membrane, said skin layer having a selective hydrogen peroxide permeability, and said immobilized enzyme membrane being arranged so that the skin layer is an extended layer and is faced to the anode and the porous layer immobilized with the enzyme is in the position of contacting with the test solution.

2. An enzyme electrode according to claim 1, wherein said membrane has a thickness of 5 to 50 μm and the skin layer has a thickness of not more than 5 μm.

3. An enzyme electrode according to claim 1, wherein said enzyme is an oxidoreductase which can react with the substrate to release hydrogen peroxide or can consume hydrogen peroxide.

* * * * *